(12) United States Patent
McAlister (10) Patent No.: US 8,441,361 B2
(45) Date of Patent: May 14, 2013

(54) METHODS AND APPARATUSES FOR DETECTION OF PROPERTIES OF FLUID CONVEYANCE SYSTEMS

(75) Inventor: Roy Edward McAlister, Phoenix, AZ (US)

(73) Assignee: McAllister Technologies, LLC, Phoenix, AZ (US)

( * ) Notice: Subject to any disclaimer, the term of this patent is extended or adjusted under 35 U.S.C. 154(b) by 0 days.

(21) Appl. No.: 12/806,634

(22) Filed: Aug. 16, 2010

(65) Prior Publication Data

US 2011/0199220 A1     Aug. 18, 2011

Related U.S. Application Data

(60) Provisional application No. 61/304,403, filed on Feb. 13, 2010.

(51) Int. Cl.
*G08B 21/00*     (2006.01)
(52) U.S. Cl.
USPC .......................................... 340/605; 340/604
(58) Field of Classification Search .................. 340/604, 340/605; 285/95–113; 73/40.5 R; 174/11 R
See application file for complete search history.

(56) References Cited

U.S. PATENT DOCUMENTS

| | | | |
|---|---|---|---|
| 5,475,772 A | 12/1995 | Hung et al. | |
| 5,882,044 A | 3/1999 | Sloane | |
| 5,969,618 A * | 10/1999 | Redmond | 340/604 |
| 6,185,355 B1 | 2/2001 | Hung | |
| 6,386,596 B1 | 5/2002 | Olson | |
| 6,446,597 B1 | 9/2002 | McAlister | |
| 6,532,315 B1 | 3/2003 | Hung et al. | |
| 6,567,599 B2 | 5/2003 | Hung | |
| 6,583,901 B1 | 6/2003 | Hung | |
| 6,584,244 B2 | 6/2003 | Hung | |
| 6,587,239 B1 | 7/2003 | Hung | |
| 6,652,006 B1 | 11/2003 | Digiacomo | |
| D505,681 S | 5/2005 | Rossman et al. | |
| 7,108,296 B2 | 9/2006 | Andre | |

(Continued)

FOREIGN PATENT DOCUMENTS

| | | |
|---|---|---|
| WO | WO 2009035647 | 3/2009 |
| WO | WO 2011004136 | 1/2011 |

OTHER PUBLICATIONS

Emery, Chris. "Princeton Engineers Make Breakthrough in Untra-Sensitive Sensor." Princeton School of Engineering and Applied Science, Published: Mar. 23, 2011. Accessed: May 18, 2011. <http://www.princeton.edu/engineering/news/archive/?id=4867>. pp. 1-4.

(Continued)

*Primary Examiner* — Jeffery Hofsass
(74) *Attorney, Agent, or Firm* — Perkins Coie LLP (57) ABSTRACT

A system and method for monitoring and/or detecting the flow of one or more fluids in a fluid system including leak detection system integral to the fluid system (e.g., at any point along a conduit, at a connection between conduits such as at a fitting assembly, etc.) configured to detect incipient, early stage levels of the leak. Based on one or more factors related to the fluid and/or the leak, the methods, devices, and systems disclosed herein can provide an indication of a suitable action or process in response to the fluid or the leak including performing preventative maintenance or providing an indication of the need of maintenance in response to the leak.

34 Claims, 8 Drawing Sheets

U.S. PATENT DOCUMENTS

| | | | |
|---|---|---|---|
| 7,134,323 B1 | 11/2006 | Discenzo | |
| 7,257,984 B2 | 8/2007 | Pidria et al. | |
| 7,287,412 B2 | 10/2007 | Ng et al. | |
| 7,692,553 B2 * | 4/2010 | Kubala | 340/605 |
| 7,823,450 B2 | 11/2010 | Sugibayashi | |
| 7,825,568 B2 | 11/2010 | Andle | |
| 7,870,787 B2 | 1/2011 | Harigai et al. | |
| 7,885,785 B1 | 2/2011 | Pekarek et al. | |
| 7,900,512 B2 | 3/2011 | Kano et al. | |
| 7,902,730 B2 | 3/2011 | Shibata et al. | |
| 7,905,209 B2 | 3/2011 | Goto et al. | |
| 7,908,661 B2 | 3/2011 | Silverbrook et al. | |
| 2002/0084793 A1 | 7/2002 | Hung et al. | |
| 2002/0131171 A1 | 9/2002 | Hung | |
| 2002/0131666 A1 | 9/2002 | Hung et al. | |
| 2002/0131673 A1 | 9/2002 | Hung | |
| 2002/0131674 A1 | 9/2002 | Hung | |
| 2002/0131686 A1 | 9/2002 | Hung | |
| 2002/0131706 A1 | 9/2002 | Hung | |
| 2002/0131756 A1 | 9/2002 | Hung | |
| 2002/0141692 A1 | 10/2002 | Hung | |
| 2002/0150375 A1 | 10/2002 | Hung et al. | |
| 2002/0151113 A1 | 10/2002 | Hung et al. | |
| 2004/0008989 A1 | 1/2004 | Hung | |
| 2008/0048448 A1 | 2/2008 | Jamison et al. | |
| 2009/0235721 A1 | 9/2009 | Robinson et al. | |
| 2009/0242405 A1 | 10/2009 | Mayer et al. | |
| 2010/0173422 A1 | 7/2010 | Koley | |

OTHER PUBLICATIONS

Steele, Bill. "Carbon Nanotube Oscillator." Cornell Chronicle Online. Published: Sep. 15, 2004. Accessed: Nov. 24, 2008. Printed: Jun. 13, 2011 <http://www.news.cornell.edu/releases/Sept04/McEuen.nanotube.ws.html>.

Yablonobitch, E. "Photonic Bandgap Based Designs for Nano-Photonic Integrated Circuits." IEEE International Electron Devices Meeting 2002 (IEDM '02). 2002. pp. 17-20.

International Search Report and Written Opinion for PCT Application No. PCT/US11/24798; Mailed on Oct. 31, 2011; Applicant: McAlister Technologies, LLC; 10 Pages.

* cited by examiner

METHODS AND APPARATUSES FOR DETECTION OF PROPERTIES OF FLUID CONVEYANCE SYSTEMS

PRIORITY CLAIM

The present application claims priority to and the benefit of U.S. Provisional Application No. 61/304,403, filed Feb. 13, 2010 and titled FULL SPECTRUM ENERGY AND RESOURCE INDEPENDENCE. Each of these applications is incorporated by reference in its entirety.

TECHNICAL FIELD

The present disclosure is directed generally to methods, devices, and systems for detecting certain materials or properties in a fluid system. More specifically, the present disclosure is directed to method, devices and systems for providing information and procedures for fluid flowing through conduits and/or conduit systems.

BACKGROUND

Fittings are used to connect two objects, such as, for example, a tube and a device that facilitates fluid communication with the tube. One example of such a device is a valve. Fittings may also be utilized to cap or plug an opening or aperture. Additionally, fittings must maintain a seal against leakage while meeting various design criteria relating to, for example, pressure, temperature, and vibration.

It may be advantageous to provide for early detection of conditions that could cause a leak or the incipient leak conditions for the purpose of instituting fail-safe operations and/or preventative maintenance.

Presently, connections between fittings may be susceptible to leakage. Leakage may cause hazardous conditions due to the escape of oxidants, odorants, pharmaceutical fluids, fuels, poisonous substances or otherwise objectionable or undesirable substances. Leakage may cause loss of valuable substances or the interruption of processes involving the accurate and adequate delivery of certain substances. In addition to degradation of an O-ring or gasket forming a seal between the fittings, leakage may result from mechanical loosening of the connection. One typical cause of loosening may be thermal cycling or vibration of a system comprising the fittings.

SUMMARY

Embodiments of the disclosure described herein are directed generally to methods, devices, apparatuses, systems, etc. for monitoring and/or detecting the flow of one or more fluids in a fluid system. Certain embodiments of the disclosure, for example, are directed to detecting a leak in a fluid system (e.g., at any point along a conduit, at a connection between conduits such as at a fitting assembly, etc.) at the early stages or incipient levels of the leak. Based on one or more factors related to the fluid and/or the leak, the methods, devices, and systems disclosed herein can provide an indication of a suitable action or process in response to the fluid or the leak. In certain embodiments, for example, systems described herein perform preventative maintenance or provide an indication of the need of maintenance in response to a leak. In other embodiments, the systems described herein can provide a gating event related to the fluid transfer in response to the leak or in response to a detected properties relating to the fluid. For example, a system can prevent a certain fluid (e.g., medication, fuel, etc.) from being dispensed if the system detects undesired properties or ingredients in the fluid, including, for example, the wrong fluid. As described in detail below, the methods, devices, systems etc. of the present disclosure utilize several different methods to detect leaks and/or fluid properties, and to relay or otherwise provide information related to the detected leaks and/or fluid properties. Accordingly, the present disclosure is directed to various different applications including, for example, medication delivery, fuel delivery, tire pressure regulation, pressurized supplies of hydrogen and/or oxygen, etc.

DETAILED DESCRIPTION

The present application incorporates by reference in its entirety the subject matter of the following US Patent Applications: U.S. Provisional Patent Application No. 60/626,021, filed Nov. 9, 2004 and titled MULTIFUEL STORAGE, METERING AND IGNITION SYSTEM; U.S. Provisional Patent Application No. 61/401,699, filed Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; U.S. patent application Ser. No. 12/806.633, filed Aug. 16, 2010and titled ELECTROLYTIC CELL AND METHOD OF USE THEREOF, now U.S. Pat. No. 8,075,750, issued Dec. 12, 2011; U.S. patent application Ser. No. 12/857,553, filed Aug. 16. 2010 and titled SUSTAINABLE ECONOMIC DEVELOPMENT THROUGH INTEGRATED PRODUCTION OF RENEW- ABLE ENERGY, MATERIALS RESOURCES, AND NUTRIENT REGIMES; U.S. patent application Ser. No. 12/857,541, filed Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, filed Aug. 16, 2010 and titled SUSTAINABLE ECONOMIC DEVELOPMENT THROUGH INTEGRATED FULL SPECTRUM PRODUCTION OF RENEWABLE MATERIAL RESOURCES; U.S. patent application Ser. No. 12/857,546, filed Aug. 16, 2010 and titled METHOD AND SYSTEM FOR INCREASING THE EFFICIENCY OF SUPPLEMENTED OCEAN THERMAL ENERGY CONVERSION (SOTEC); U.S. patent application Ser. No. 12/857,228, filed Aug. 16, 2010 and titled GAS HYDRATE CONVERSION SYSTEM FOR HARVESTING HYDROCARBON HYDRATE DEPOSITS; U.S. patent application Ser. No. 12/857,515, filed Aug. 16, 2010 and titled APPARATUSES AND METHODS FOR STORING AND/OR FILTERING A SUBSTANCE, now U.S. Pat. No. 8,147,599, issued Apr. 3, 2012; U.S. patent application Ser. No. 12/857,502, filed Aug. 16, 2010 and titled ENERGY SYSTEM FOR DWELLING SUPPORT; U.S. patent application Ser. No. 12/857,433, filed Aug. 16, 2010 and titled ENERGY CONVERSION ASSEMBLIES AND ASSOCIATED METHODS OF USE AND MANUFACTURE; and U.S. patent application Ser. No. 12/857,461, filed Aug. 16, 2010 and titled INTERNALLY REINFORCED STRUCTURAL COMPOSITES AND ASSOCIATED METHODS OF MANUFACTURING.

Methods, devices, apparatuses, systems, etc. for providing information relating to the flow of fluids through a fluid system are described herein. In certain embodiments, these methods and systems provide a "tattletale" or other type of indication related to properties of a fluid, conditions of the flow of the fluid, leakage of the fluid, and/or any other properties or characteristics associated with the fluid. As used herein, the term fluid is intended to describe any type of flowable material, including, for example, liquids, gases, plasmas, etc.

In certain embodiments, the methods and systems disclosed herein provide an indication that a fluid is leaking from a system that is transporting the fluid. For example, the methods and systems include sensors or indicators that determine when leak is occurring and provide an indication, such as a signal or an alarm that the fluid is leaking. Moreover, as described in detail below, the indication of the leak can be provided at the very early stage or incipient levels of the leakage. Moreover, the methods and systems described herein can detect the leakage in response to an interrogation signal directed at the sensor or indicator. In this manner, the embodiments described herein can provide an early detection to an undesirable leak, or any other property or condition associated with the fluid. Thus, instead of waiting for an odorant in natural gas or propane to infiltrate the atmosphere of a dwelling before an unsuspecting person wakes up and happens to not have a head cold and perchance smells the "rotten-egg" odor and becomes consciously alarmed, the present disclosure provides for prevention of such delays by providing an indication or alarm at the incipient leak stage. In certain embodiments, the methods and systems can determine the incipient leak stage with a comparatively miniscule number of molecules of the fluid that have passed a seal and therefore caused an immediate alarm and/or request for maintenance. Moreover, the degree of urgency and corresponding appropriate response can be conditioned according to the trend indicated by leak-rate analysis and comparative evaluation of the particular chemistry involved. If the system detects a leak rate of a sufficient magnitude, for example, the system may provide an indication that immediate maintenance is required. If the system detects a leak rate below a predetermined magnitude, however, the system may provide an indication that a leak exists, but that immediate maintenance may not be required. In addition, and as explained in detail below with reference to embodiments of the disclosure, a system can detect, analyze, or otherwise measure certain properties of the fluid to determine a gating event for the fluid flow. For example, if the system detects impurities in a fuel, or if the system detects the wrong type of fluid, the system may stop the fuel from flowing or change the flow rate of the fluid.

Figure 1A:
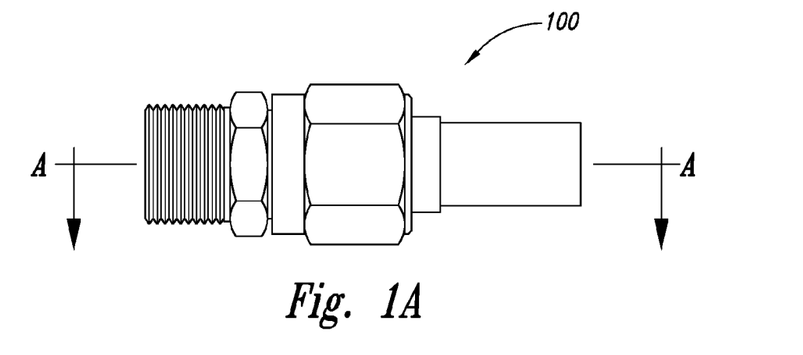
FIG. 1A is a side view of a fitting assembly configured in accordance with an embodiment of the disclosure.
Figure 1B:
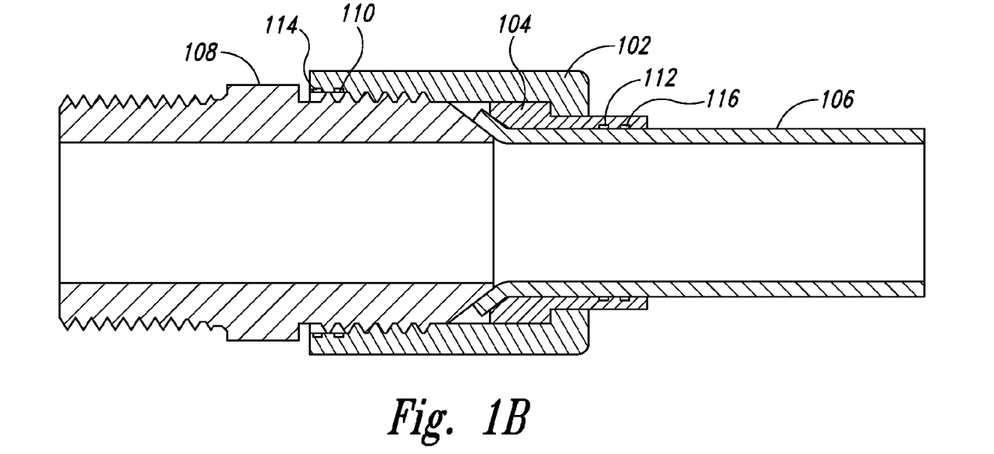
FIG. 1B is a cross-sectional side view taken substantially along the line A-A of FIG. 1A.
Figure 1C:
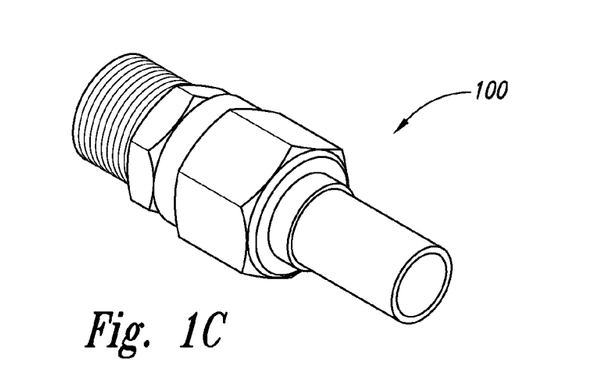
FIG. 1C is an isometric view of the fitting assembly of FIG. 1A.

In certain embodiments, the methods and systems disclosed herein include an indicator or sensor that is used in a fitting assembly, such as a fitting assembly attaches to one or more conduits. FIG. 1A, for example, is a side view of a fitting assembly 100 including an indicator configured in accordance with an embodiment of the disclosure. Although several features of the disclosure are described below with reference to the fitting assembly 100, these features can be used with any type of fluid conveying system, including, for example, flexible conduits, rigid conduits, hoses, plugs, nozzles, sprayers, filters, catheters, intravenous conduits, syringes, needles, tire tubes, inner tubes, and/or any other type of component associated with fluid conveying systems or devices. Returning to the Figures, FIG. 1B is a cross-sectional side view of the assembly 100 taken substantially along the line A-A of FIG. 1A, and FIG. 1C is an isometric view of the fitting assembly 100. Referring to FIGS. 1A-1C together, in the illustrated embodiment, the assembly 100 includes a male connector 108 that mates with or attached to a female connector 102 to provide an attachment to a conduit 106. The assembly 100 further includes a "tattletale" element, such as a sensor or an indicator for providing an alarm or other type of indication relating to a fluid flowing through the assembly 100. In the illustrated embodiment, for example, the indicator is carried by the assembly 100 in the vicinity of the connection formed by the male connector 108 and the female connector 102. More specifically, one or more indicators can be carried by the assembly at the locations indicated at 110, 112, 114, and/or 116, as shown in FIG. 1A on the male connector 108 and the female connector 102. Moreover, the male connector 108 and the female connector 102 can include features configured for attachment to or compatible for use with tapered pipe threads, flared, or compression fittings, or other types of conduits. For example, the first part or male connector 108 may include one or more threaded end portions that are axially aligned about a central longitudinal axis of the assembly 100. The second part or female connector 102 may have a female threaded section 110 that can also be axially aligned about the central longitudinal axis. Moreover, in the illustrated embodiment the assembly 100 is attached to the conduit 106 having a flared end portion mated against a corresponding surface of the male connector 108. The assembly 100 also includes a compression seal 104 positioned between the female connector 102 and the conduit 106. When assembled, the female connector 102 urges the compression seal 104 and the flared portion of the conduit 106 tightly against the male connector 108.

In certain embodiments, the tattletale element or indicator can include any type of detector or sensor to detect if and/or when a seal between the fitting assembly 100 and the conduit 106 has failed and leakage of a fluid is beginning to occur. The indicator can provide a visible indication of the leakage, for example, to allow a user to visually inspect the assembly 100 for a leak. For example, the indicator can provide a colored indication of a leak. More specifically, the indicator can release a colored dye upon activation by leaked fluid (e.g., contact with a leaked fluid) or contact with an activation agent that has been added to the fluid flowing through the assembly 100. In certain embodiments, for example, a halogen such as iodine, chlorine, and/or fluorine in water could be the activating agent that reacts with the indicator and causes the release of a liquid (or other indication) from tattletale element indicator 104. In such embodiments, after collecting or contacting relatively few molecules of leaked fluid, the indicator can provide a magnified signal. The signal can include, for example, a readily detectable color, fluorescence, phosphorescence, etc. Moreover, other alarms or tattletale triggering events can include other signals such as radio signals emitted by the indicator resulting from a change in capacitance, resistance, and/or a magnetic field in the indicator induced by the fluid contacting or leaking by the indicator 104.

In another example, the indicator can provide an indication of incipient leakage in response to a transmission of an interrogation signal directed at the indicator 104. In these embodiments, the tattletale component indicator senses chemical, physical, optical, radio, sound, or thermal information to detect incipient leakage and transmit an indication of the leakage. Moreover, the detector can transmit a request for preventative maintenance signals or otherwise interact to an interrogation signal with a reply request for preventative maintenance. Such transmission of data to or from the indicator can include information such as the fitting location, identification, type of fluid, rate or amount of leakage, history of application, etc.

Figure 2A:
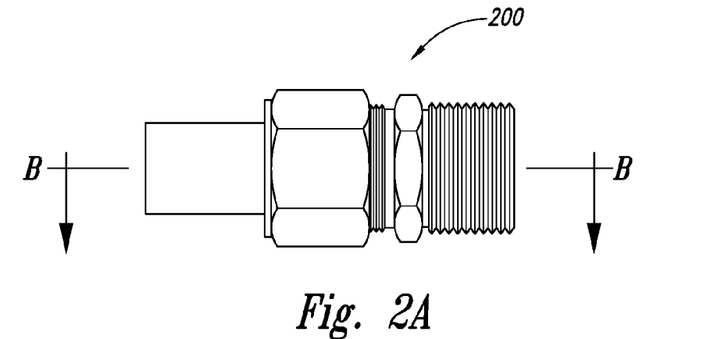
FIG. 2A is a side view of a fitting assembly configured in accordance with another embodiment of the disclosure.
Figure 2B:
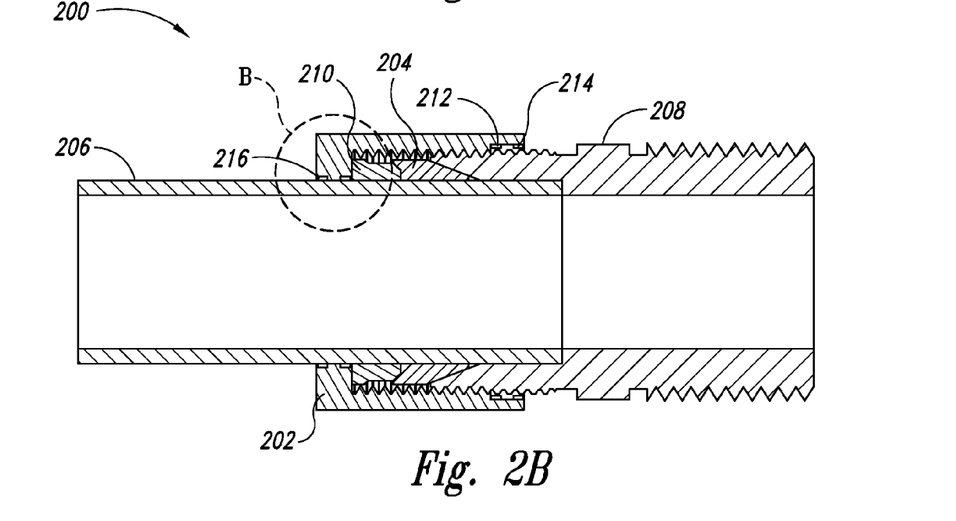
FIG. 2B is a cross-sectional side view taken substantially along the line B-B of FIG. 2A.
Figure 2C:
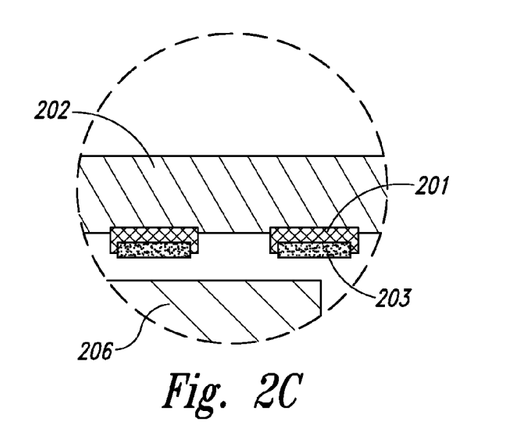
FIG. 2C is an enlarged detail view of detail B of FIG. 2B.
Figure 3:
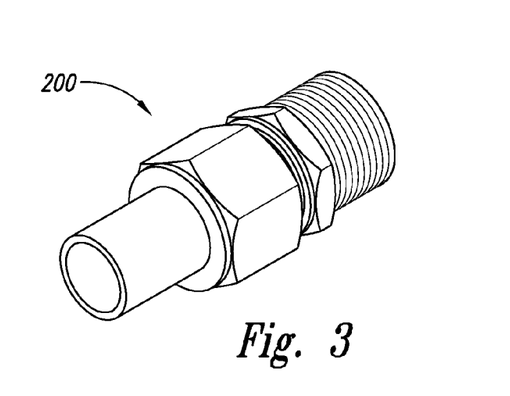
FIG. 3 is an isometric view of the fitting assembly of FIG. 2A.

In certain applications, the indicator includes sensing miniature, micro or nano circuitry, for example at locations 112 and/or 110. The circuitry can be activated by a photovoltaic material that is carried by the assembly 100 proximate to the indicator, for example at locations 114 and/or 116. Consequently if incipient leakage is detected by the detector with a sensor circuit at locations 110 and/or 112, ambient light or an interrogation light source can provide photovoltaic power to the photovoltaic material at locations 114 and/or 116 to activate the circuit at 110 and/or 112. In this manner, the indicator can provide a radio signal or serve in a circuit as a ring oscillator to develop an incipient leak signal that is broadcast or interrogated by non-contact means, including, for example, radio waves or infrared. The following references related to microelectronics, which are incorporated herein in their entireties by reference: http://news.bbc.co.uk/go/pr/fr/-/2/hi/science/nature/4839088: http://www.bio-medicine.org/biology-technology-1/Toward-worlds-smallest-radio-3A-nano-sized-detector-turns-radio-waves-into-music-1330-1/: University of California at Berkeley Physics Department— Nanotube Radio: Supplemental Materials: ScienceDaily.com—"First Fully-functional RadioFrom A Single Carbon Nanotube Created": PhysicsOrg.com—"Make Way for the Real Nanopod: Researchers Create First Fully Functional Nanotube Radio" and http://www.nanowerk.com/spotlight/spotid=3080.php FIG. 2A is a side view of another assembly 200 configured in accordance with an embodiment of the disclosure. FIG. 2B is a side cross-sectional view taken substantially along the line B-B of FIG. 2A, FIG. 2C is an enlarged detail view of detail B of FIG. 2B, and FIG. 3 is an isometric view of the assembly 200. Referring to FIGS. 2A-3 together, the illustrated assembly 200 is configured for compression sealing a tube 206 to a fitting 208. For example, compression of an annular seal 204 is established by tightening of a nut 202 to force axial motion of seal element 204 into the conical receiver at an end of the fitting 208 and to be at least partially swaged to form at least a line of contact seal against tube 206 and a corresponding line of contact seal against the fitting 208. The assembly 200 also includes a tattletale sensor or indicator 210 that can be positioned near or on the seal element 204. The indicator 210 serves as an early tattletale indicator of incipient leakage to delineate and/or broadcast an appropriate maintenance request signal or otherwise provide an indication of a leak in the assembly 200.

In certain embodiments, the assembly 200 can also include one or more detectors at locations indicated at 212, 214, and/or 216, as shown in FIG. 2B. In conjunction with detector 212 and/or 214, component 216 may be responsive to visible, UV, and/or microwave radiation when interrogated to relay and/or otherwise participate in a preventative maintenance signal or request. This enables quick inspection with an illuminating and/or activating light source that detects any distinguished signal from the one or more detectors.

As shown in FIG. 2C, the assembly 200 can also include a detector with one or more leak collectors 203 proximate to one or more miniature circuits 201. The circuits 201 can provide a signal by means selected from the technologies disclosed herein. Miniature, micro, or nanocircuits may similarly be located on or within other suitable locations in the assembly 200, including, for example on a nut 202 as needed to provide redundant assurance of leak detection and signal delineation at the earliest incidence or indication of a leak.

Figure 4A:
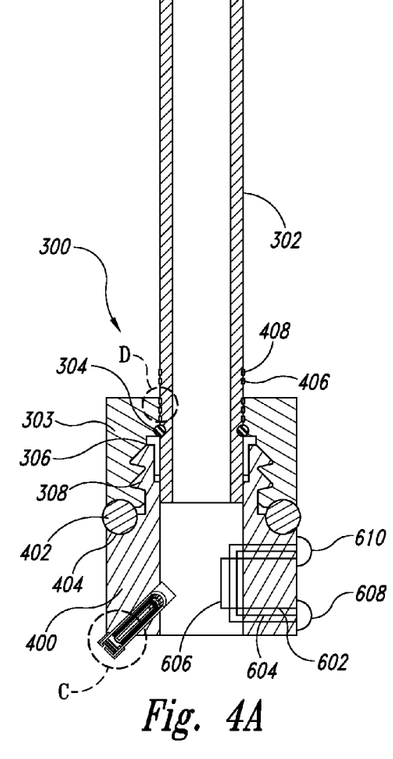
FIG. 4A is a side cross-sectional view of an assembly configured in accordance with yet another embodiment of the disclosure.
Figure 4B:
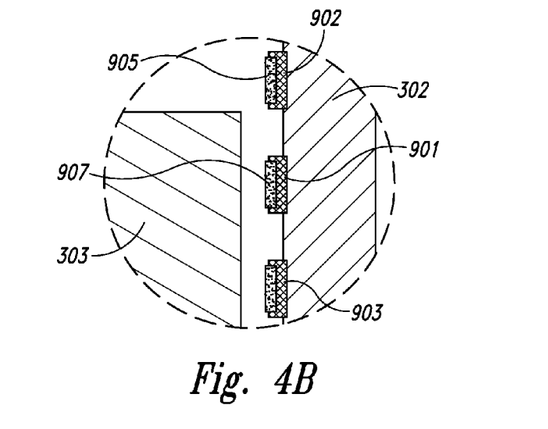
FIG. 4B is an enlarged view of detail B of FIG. 4A.
Figure 4C:
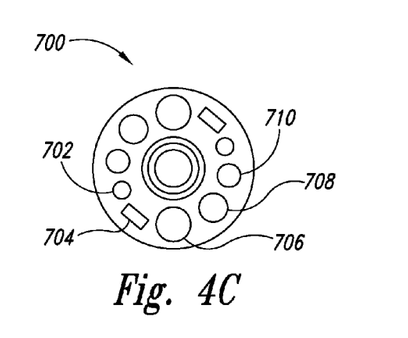
Figure 4C is an enlarged view of detail C of FIG. 4A.
Figure 5:
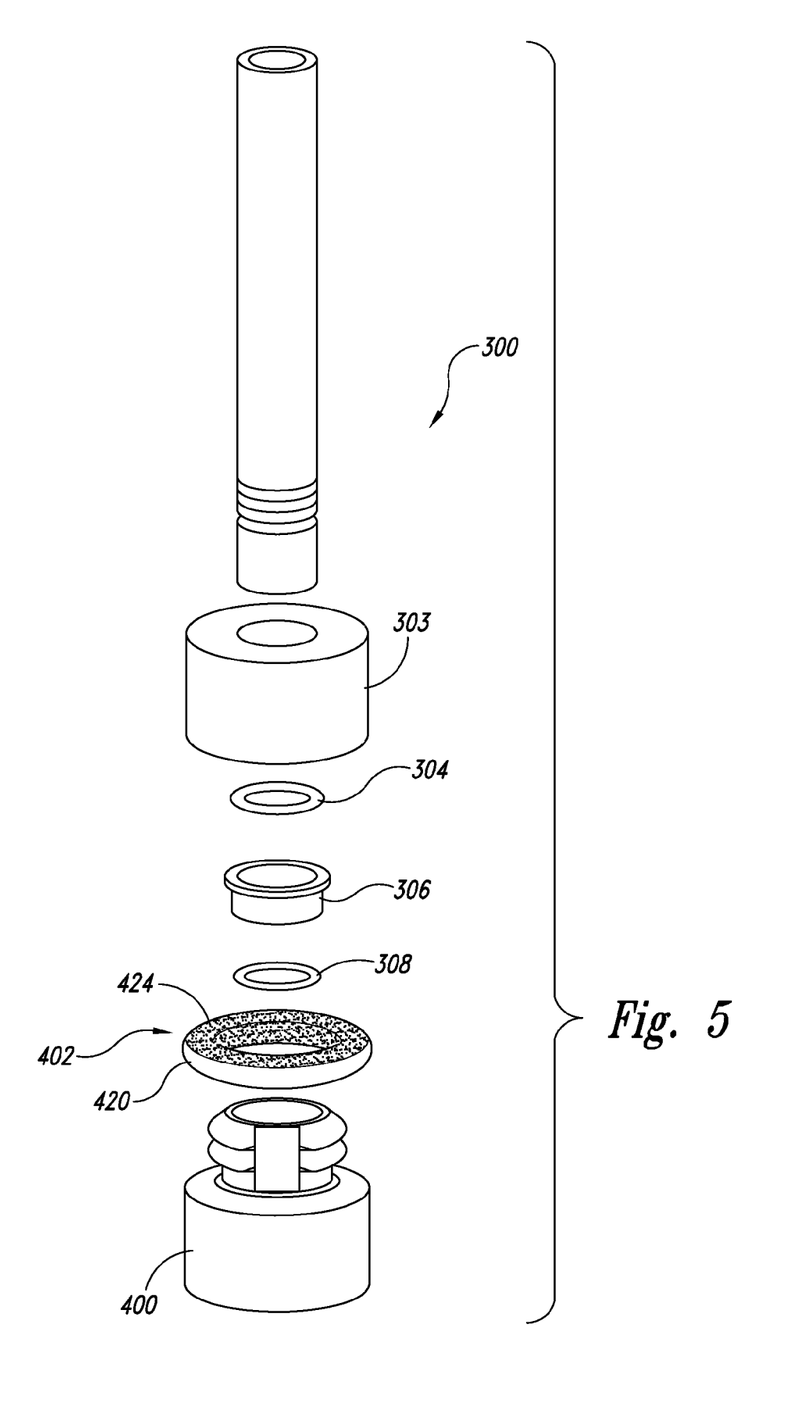
FIG. 5 is an exploded view of the assembly of FIG. 4A.

FIG. 4A is a side cross-sectional view of an assembly 300 including one or more detectors, indicators, sensors, etc. configured in accordance with another embodiment of the disclosure. FIG. 4B is an enlarged view of detail D of FIG. 4A, and FIG. 4C is an enlarged view of detail C of FIG. 4A. FIG. 5 is an exploded view of the assembly 300 of FIG. 4A. Referring to FIGS. 4A-5 together, the assembly 300 includes a multifunction elastically deformable seal and status indicator 402, an elastomeric ring seal 308, a ring seal support 306, and a lock ring 304. Illustratively, as shown in FIGS. 4A and 5, the annular seal 402 may be made of relatively soft closed cell sponge polymer with a generally oval cross-sectional shape before it is reformed into another cross section such as shown in FIG. 4A. An annular groove is provided in tube 302 to receive lock ring 304, which is restrained from expansion by an annular gland of nut 303 as shown. The seal support 306 rests against the nut 303 to support and urge the seal 308 to reform and seal against the annular gland of a fitting 400 and a tube 302 to provide an assured leak free seal that continues to perform even if support 306 is moved considerable axial distance as shown.

The status indicator 402 provides a means for one or more preventative maintenance signals the fitting 400 is axially displaced from the cap 303 thereby also causing axial displacement of the seal ring 308, the support 306, and/or the tube 302. Illustrative means for providing a preventative maintenance signal include the use of at least one different texture or color in different regions of the status indicator 402. For example, a first region 420 and/or and a second 424 can have different colors, such as white for region 420, and red for region 424. Thus if visual inspection detects a red color next to the white color on status indicator 402, the status indicator 402 is providing a signal or indication of a leak or other need for preventative maintenance.

Another suitable means for indicating a preventative maintenance signal consists of placing miniature, micro or nano circuitry at locations 901 and 902, as shown in FIG. 4B. One or more leak accumulators or concentrators 905, 907 provide signal magnification for early detection and activation of a maintenance request or alarm signal. Circuitry at 902 can be activated by a photovoltaic-powered circuit. Consequently if sensor circuits or detectors detect incipient leakage at locations 901 or 903, ambient light or an interrogation light source provides photovoltaic power to activate a radio signal or to serve in a circuit as a ring oscillator to develop an incipient leak signal that is broadcast or interrogated from the detector(s) by non-contact means such as radio wave or an infrared stimulator.

According to further embodiments of the disclosure, additional or backup locations for placement of miniature, micro or nano circuitry is shown at locations 406 and/or 408, which can be activated by a photovoltaic circuit. Consequently if a sensor circuit or detector senses incipient leakage at locations 406 and or 408, the detector can initiate a radio signal or trigger participation in a circuit as a ring oscillator to develop an incipient leak signal that is broadcast or interrogated by non-contact means such as radio wave or an infrared stimulator.

Additional embodiments of the disclosure directed to detecting incipient leakage with surface-active substances that enhance or depress the wetability of areas or regions where detection of a leak or other fluid properties is desired. In FIG. 5, for example, applying hydrophobic substances and/or hydrophilic substances to the status indicator 402 (e.g., an o-ring) can provide a concentration of fluid at different locations on the status indicator 402. Indicators configured in accordance with these embodiments can use these different concentrations can to emit or otherwise generate a warning signal. More specifically, referring to the status indicator 402 of FIG. 5, a hydrophobic substance can be applied at an external equatorial strip region or band 420 of the status indicator 402 to at least partially prevent incipient leak molecules from adhering to the band 420 (e.g., the band being "wetted" from the incipient leak molecules). Moreover, a hydrophilic substance can be applied to the remainder of the interior portion 424 of the status indicator 402 surrounding the band 420 to promote wetting of the interior portion 424 to enable numerous leak concentration and signal generation locations. In one embodiment, for example, in response to hydrophilic wetting the exterior band 420 and the interior portion 424 can provide a color change, release an odor or aromatic molecules that are more readily detectable by an odor detector in a sensor circuit 901 or 903 in response to parts per billion or parts per million concentrations on the hydrophilic detection surface, and/or provide electrical or electro-optical signal generation from the status indicator. As will be appreciated by one of ordinary skill in the relevant art, the portions of the status indicator 402 (or any other indicator disclosed herein) having different wetability characteristics are not limited to the configuration illustrated in FIG. 5.

Another embodiment of the disclosure provides hydrophobic wetting capability similar to the minute fuzz (or other types of surface textures) that covers a peach that promotes wetting in some areas and prevents or inhibits wetting in other areas. More specifically, an indicator can include a surface having a texture or treatment that causes a fluid (e.g., water) to bead or wet in certain areas and prevent wetting in other areas to thereby concentration the rejected fluid for wetting an adjacent area. In this manner, the indicator can use the concentrated fluid to generate a maintenance signal at lower concentrations of incipient leakage molecules. In the Figures, for example, surface treatments of detectors at locations 406, 408, or on the status indicator 402 at locations 420 and/or 424, can include area having different wettability characteristics. In certain embodiments, for example, detectors or sensors at these locations can include hydrophobic dots that are adjacent to hydrophilic dots. In certain embodiments, for example, these regions can include a thin transparent film of titania that is exposed or otherwise receives ultraviolet interrogation light. In certain embodiments, activation with ultraviolet light provides wetability by alcohol, water and oils. Appropriate activation of the thin film of titania may thus produce a field of nanoscale domains where hydroxyl molecules become adsorbed to provide wetability for water and water solutions and the adjacent areas provide wetability for oils and oil solutions. The titania films according to these embodiments can be altered to react to specific stimuli. For example, the titania films may be doped with nitrogen, silver, silicon or other semiconductor enhancements to decrease the band gap and customize the interrogation light activation at a longer wavelength to provide an indication of incipient leakage and/or information regarding the types of molecules involved or other properties of a fluid.

According to another embodiment of the sensors or detectors disclosed herein, the detectors can concentrate portions of the fluid of interest with capillary wicking. For example, detectors or sensors configured in accordance with embodiments of the disclosure may include nano-wicking structures having closely spaced pores in such substrates as silica, titania, and carbon. Capillary wicking of leakage molecules of a fluid accumulates or concentrates them for more intense signal generation. For example, the concentrated fluid molecules can provide an enhancement of light reflectivity, transmissivity, or absorptivity as a characterizing type of signal discrimination, or alternatively anti-reflectivity as a discriminating means for development of signal generation. Concentrating or magnifying the presence of detectable molecules provides a very early indication of incipient leakage. Moreover, an intelligent interrogation procedure that takes leak-rate trend and ambient conditions into account enables much greater safety and assured confidence in systems that store and/or convey highly valuable, dangerous, objectionable, or annoying fluids.

Another application of the "watch-dog" or "traffic-cop" indicators and sensors disclosed herein for preventative maintenance provisions is to provide for identification, verification, and appropriate action or alarm procedures upon detection of specific ingredients or constituents of a fluid. For example, the sensors and detectors disclosed herein can detect specific ingredients in a fluid, such as critical components of a prescribed medication formula, or conversely, potentially harmful substances such as aflatoxins, mycotoxins, or ochratoxins in a fluid medium. In this instance a fluid conveyed by the conduit 302 is monitored by comparison of the UV, visible, and/or IR signal initiated at an emitter 608 and transmitted to a reader 610 that includes a miniature, micro, or nano radio transceiver to provide an appropriate function command or alarm. The emitter 608 and the transmitter 610 can be carried by the assembly 300. In certain embodiments, one or more fiber optic components or light pipes 602, 604, 606 can transmit an interrogation frequency between the emitter 608 and the transceiver 610. The light pipes 602, 604, 606 can incorporate selected surface materials with a known index of refraction and/or other optical properties that provide signal generation by adherence or adsorption of certain molecules that are being monitored in the fluid. Comparative analysis of the rate that optical properties change provides an analytical or inferred determination of the concentration of monitored molecules in the fluid medium under surveillance. Numerous different selective surfaces may be provided at different locations or on separate fiber optic components 602, 604, 606. In some instances, the fluid being delivered by conduit 302 may be slowed or stopped by a valve such as 764 (FIG. 7) to provide time for signal intensification of the monitored substance. Comparison of the diffusion pattern, attenuation, enhancement, or reinforcement of selected radiation frequencies that are used as interrogation signals in the light pipes 602, 604, 606 enable identification, verification and appropriate action or alarm procedures.

Figure 4D:
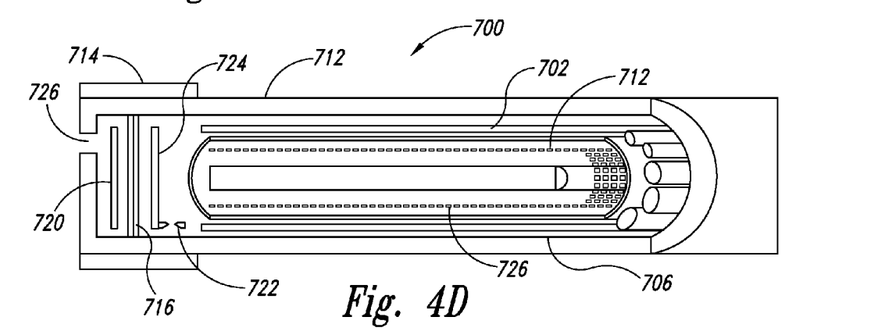
FIG. 4D is an enlarged side cross-sectional view of detail C of FIG. 4A.
Figure 7:
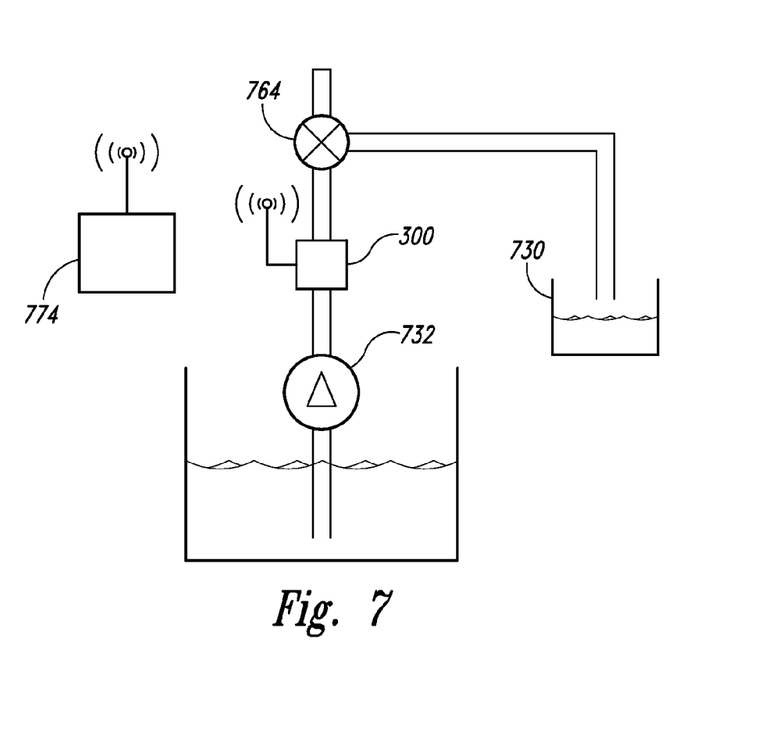
FIG. 7 is a schematic view of an environment for use with a detector configured in accordance with an embodiment of the disclosure.

FIG. 4C is an enlarged cross-sectional side view of a tubular system 700 carried by the assembly 300 shown in FIG. 4A, FIG. 4D is a side cross-sectional view of the tubular system 700, and FIG. 7 is a schematic view of an environment for use with a detector 300 configured in accordance with an embodiment of the disclosure. Referring to FIGS. 4C, 4D, and 7 together, in another embodiment a fluid sample in the conduit 302 is admitted in the tubular system 700 including a selection of capillaries 702, 704, 706, 708, 710, etc., having various surface treatments, geometries, shapes, and dimensions as shown in Detail C of FIG. 4C. Molecules of a specific interest, such as an intended or adverse agent including, for example, the analyte family of poisons are selectively identified after being sequestered in such capillaries 702, 704, 706, 708, 710 from a fluid such as water, milk, or soymilk by appropriate methods such as those disclosed in U.S. Pat. Nos. 4,859,611; 4,181,853; 5,178,832; or U.S. patent application Ser. No. 10/245,758, each of which is incorporated herein by reference. Between cyclic sequestration and indication of monitored substances or molecules, the capillaries 702, 704, 706, 708, 710 can be cleared by admission of an appropriate cleaning solvent and/or by expulsion with hydrogen and/or oxygen. For example, depending upon preferences regarding the monitored substance, such hydrogen and/or oxygen may be generated by miniature electrolysis cell 720 or by a larger electrolysis cell or another storage provision that delivers pressurized hydrogen and/or oxygen into the capillaries 702, 704, 706, 708, 710.

FIG. 4C shows the enlarged cross section of the tubular system 700 with illustrating the capillaries 702, 704, 706, 708, 710 of various sizes and shapes. FIG. 4D illustrates a longitudinal section 700 of the tubular packaging arrangement of system 700, and includes a photovoltaic semiconductor 714 or some other suitable source of electricity to power the testing procedures performed by system 700. In the system 700, fluid samples travel various distances in the capillaries 702, 704, 706, 708, 710 depending upon the viscosity, surface tension, and wetability produced by the material selection, dimensions, geometry and coatings that may be applied to the capillaries 702, 704, 706, 708, 710. One or more detectors 726, such as photo-optic readers and/or sensors, can contact the sample fluid to identify and report by wireless communication to a controller 774 (FIG. 7) which includes a wireless relay or transponder for producing the appropriate alarm, fail-safe activity, or verification information.

In instances that expedited clearing of 702, 704, 706, 708, 710 is advantageous, for example as part of a quick cycle for fail-safe monitoring, a mixture of hydrogen and oxygen can be produced by an electrolyzer 720, ignited by application of a spark plasma at 722, and combusted to provide a rapid pressure rise and purging of the capillaries 702, 704, 706, 708, 710. Such mixtures may be provided by mixing the outputs of the anode and cathode of the electrolyzer 720, or by reversing the voltage applied to the electrodes of the electrolyzer 720 to alternately produce hydrogen and oxygen. Controlling the time and current magnitude during such voltage reversals provides control of the proportions of oxygen and hydrogen in the mixture that is formed. Moreover, isolating one of the electrodes from participation in the purging operation by a separator membrane 716 enables such occasionally reversed voltage and current application to the other electrode 724 to provide mixtures that may be stoichiometric or enriched with hydrogen or oxygen for purposes such as reducing the peak combustion temperature, providing neutral, oxygen-rich oxidizing steam, or hydrogen-rich reducing steam for specific cleaning performances during the purging operation of the capillaries 702, 704, 706, 708, 710.

If a more or less stoichiometric mixture of hydrogen and oxygen is combusted, a small amount of water may be formed and expelled and condensed mostly in the fluid within the conduit 302 and the vacuum that is created in cleared capillaries 702, 704, 706, 708, 710 by the phase change contraction and resulting volumetric shrinkage provides rapid reloading of monitored substance samples. In instances where oxygen remains in the capillaries, hydrogen may be generated and combined with such oxygen to form steam. If hydrogen remains in the capillaries, oxygen may be generated and combined with such hydrogen to form steam in a procedure to standardize or normalize the test cycle.

Referring to FIG. 7, which shows a compressor or pump 732, the conduit 302, the tattletale fitting indicator 300, the controller 774, a valve 764, and delivery to collector 730. In the illustrated embodiment, if detectors or sensors 300 indicate a threshold concentration of a leak, an unwanted substance, or any other property of a fluid flowing through the conduit 302, the detector 300 can generate an alarm so that the flow through conduit 302 may be stopped or diverted into a collection conduit by valve 764 as shown in FIG. 7. In certain embodiments, the indicator 300 can wirelessly transmit the signal or alarm to the controller 774. This provides protection and/or sample collection for various purposes including removal, later reference, and/or validation testing.

Figure 6:
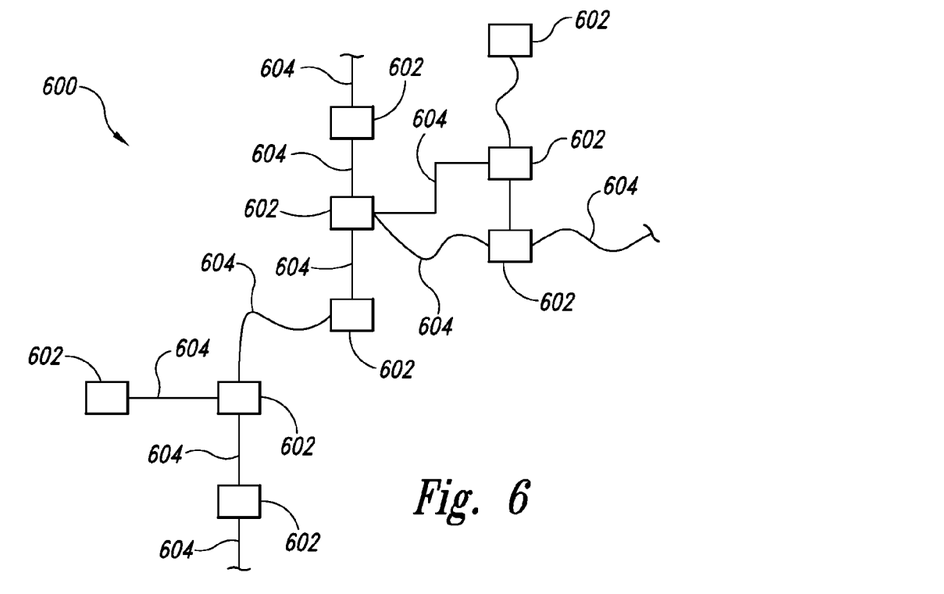
FIG. 6 is a schematic diagram of a fluid conduit system configured in accordance with an embodiment of the disclosure.

FIG. 6 is a schematic diagram of a fluid conduit system 600 configured in accordance with an embodiment of the disclosure. In the illustrated embodiment, the system 600 includes a plurality of fluid conveying conduits 604 that are joined to one another with corresponding fitting assemblies 602. The fitting assemblies 602 can also cap the end of a conduit 604. The fitting assemblies 602 in the illustrated system 600 can be generally similar to the fitting assemblies and associated components described above with reference to FIGS. 1A-5B. For example, the fitting assemblies 602 can include a male connector having retention features that rotatably engage corresponding engagement features of a female connector. According to another feature of the illustrated system 600, the conduits 604 can be generally straight or curved conduits. For example, the generally straight conduits 604 can include hard drawn tubes or pipes, and the curved conduits 604 can include annealed or soft tubes or pipes, or other flexible types of conduits. The conduits 604 of the illustrated embodiment can be configured to be suitable for conveying or transporting various types of fluids (e.g., liquids, gases, etc.), for covering electrical cables or lines, or for any other application where conduits are commonly used. Moreover, the conduits 604 can be made from metallic, plastic, or any other suitable material.

Figure 8:
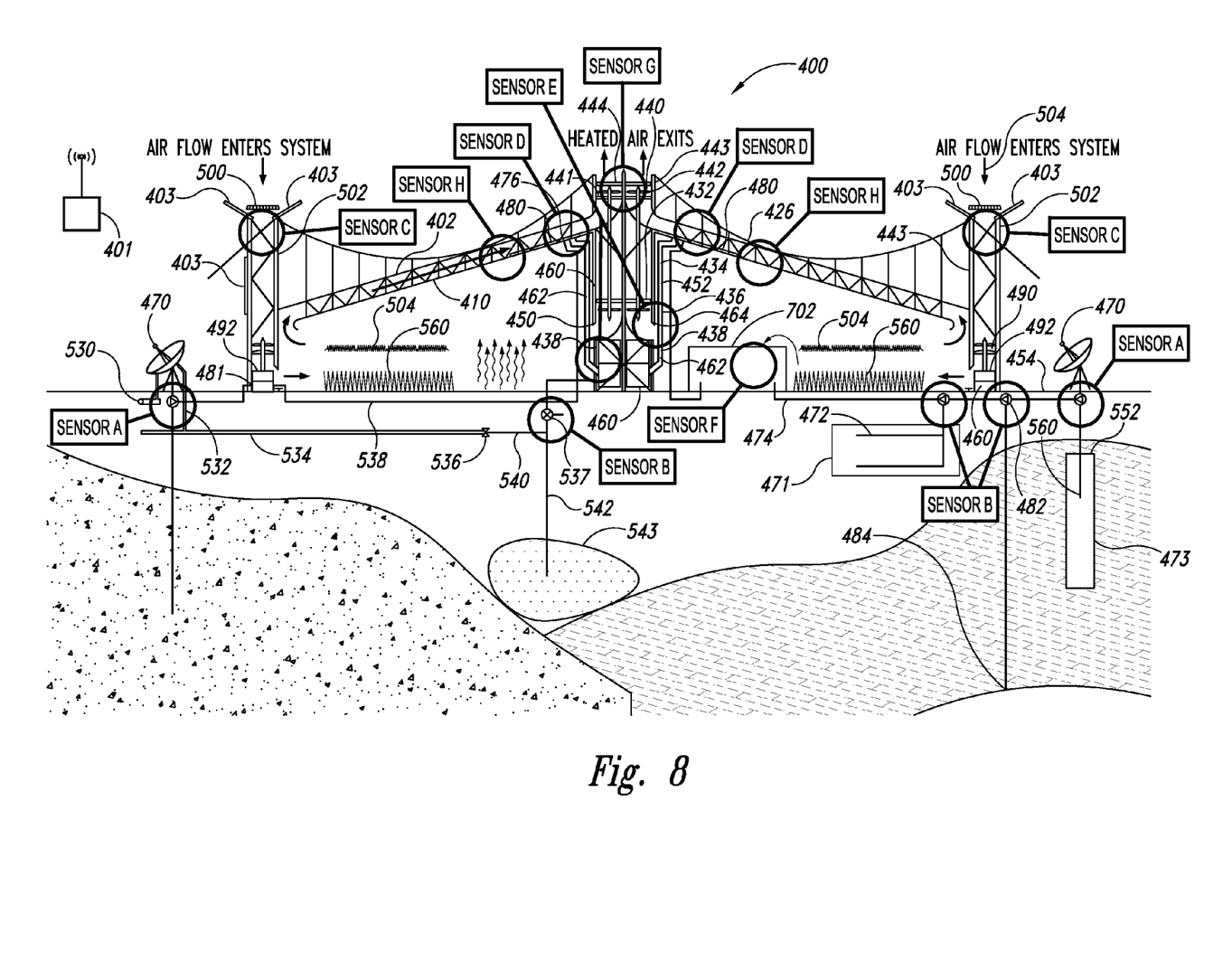
FIG. 8 is a schematic view of energy production installation configured in accordance with an embodiment of the disclosure.

FIG. 8 is a schematic view of energy production installation configured in accordance with an embodiment of the disclosure. As shown illustratively in FIG. 8, various sensors can combine to provide quality control and assurance of components of a system. Sensors A-H may further be remotely monitored and controlled by central control unit 401. According to one embodiment, sensors A-H may monitor the following system characteristics:

Examples of Sensors Monitoring Working Fluids in Full Spectrum Installation (Tattletale)

Sensor A Monitoring the characteristics of working fluid(s) (temperature, gaseous/liquid state, fluid composition, and so on) at the site of solar thermal devices adding solar heat to hydrogen donor;

Sensor B Monitoring characteristics of working fluid(s) (temperature, gaseous/liquid state, chemical content, and so on) of working fluids moving into and out of geothermal storage;

Sensor C Monitoring characteristics of working fluid(s) (temperature, humidity, etc) entering the system;

Sensor D Monitoring characteristics of working fluid(s) (temperature/energy) at heat exchangers;

Sensor E Monitoring characteristics of working fluid(s) in the exhaust stream of internal combustion engines at the insulated exhaust pipes;

Sensor F Multiple sensors within an electrolyzer (see earlier drawing for examples) monitoring characteristics of working fluid(s) (temperature, gaseous/liquid state, fluid composition, chemical content, and so on);

Sensor G Monitoring characteristics of working fluid(s) (temperature/energy, humidity, and so on) in the updraft conduit at the site of turbines;

Sensor H Monitoring characteristics of working fluid(s) (temperature, humidity, gaseous content, and so on) in agricultural micro-climates.

Figure 9:
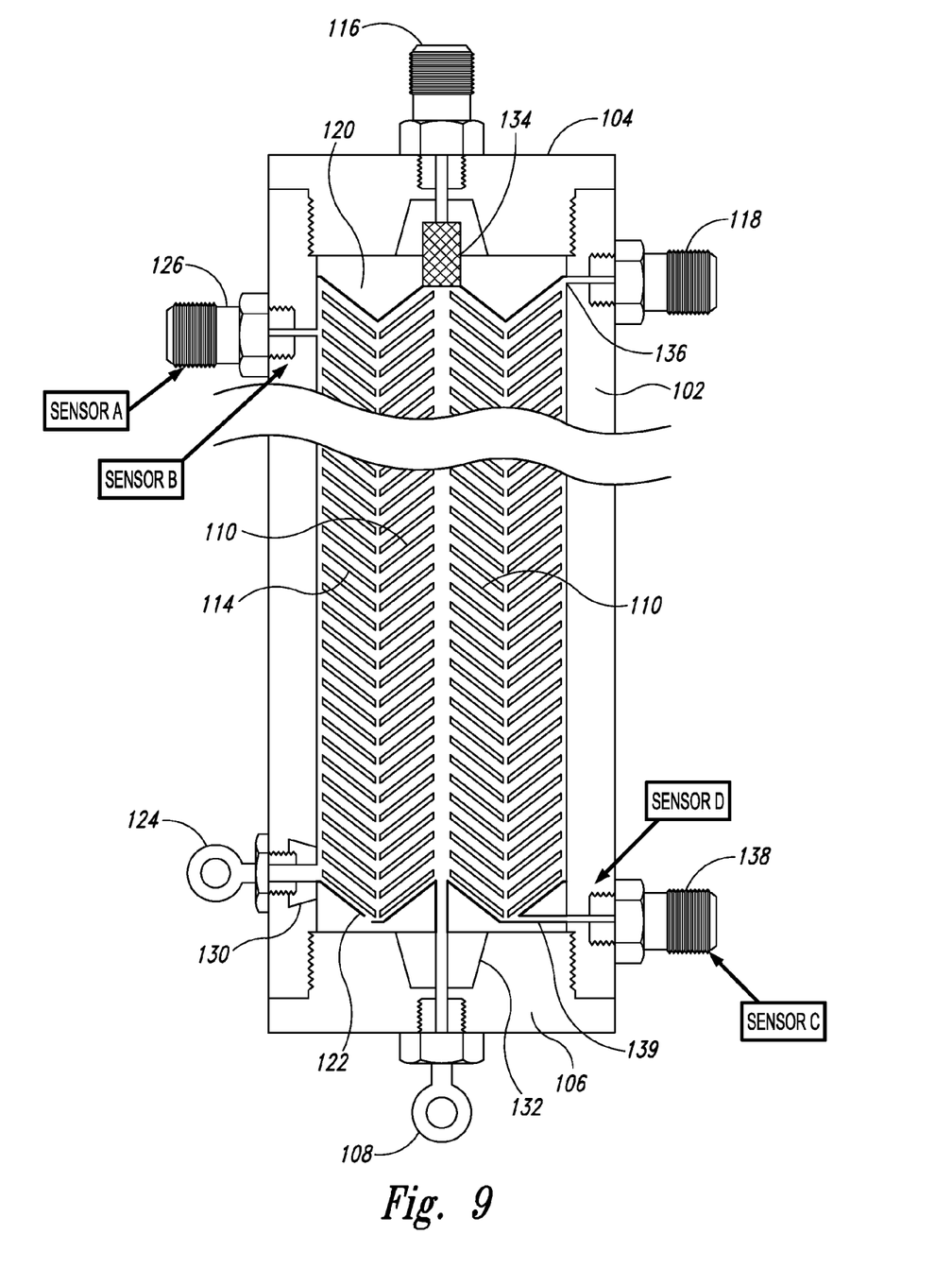
FIG. 9 illustrates an electrolytic cell which incorporates sensors in accordance with yet another embodiment of the disclosure

FIG. 9 illustrates an electrolytic cell in accordance with co-pending applications disclosed and incorporated by reference above having at least one of a sensor in accordance with the present disclosure incorporated therein. In the exemplary embodiment, Sensor A is positioned outside the vessel monitoring the connector; Sensor B is positioned inside the vessel monitoring the electrolyte flow into the vessel at the upper portion of the vessel; Sensor C is positioned outside the vessel monitoring the connector; and Sensor D is positioned inside the vessel monitoring the electrolyte flow from the vessel at the lower portion of the vessel.

In operation, Sensors A and C are connector-sensors which watch for plumbing leaks at high pressure, provide early warning of incipient leaks and are used to monitor the integrity of the high pressure system. Sensors B and D are fluid-sensors (liquids and gases) which differentially monitor and provide feedback on the chemical contents within the electrolyzing vessel at various locations.

Figure 10:
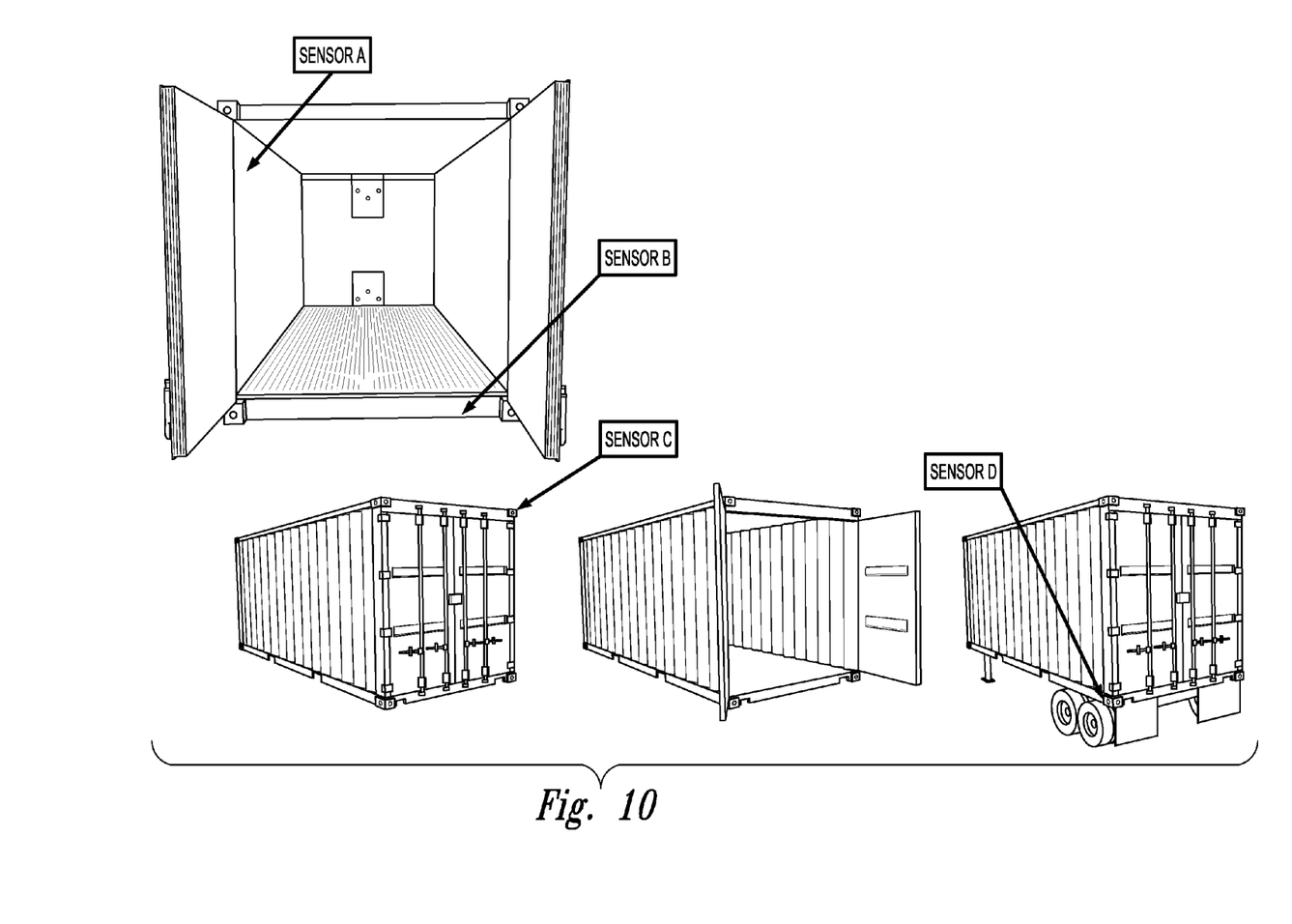
FIG. 10 illustrates yet another environment which incorporates sensors in accordance with yet another embodiment of the disclosure.

FIG. 10 illustrates yet another environment which incorporates sensors as disclosed herein. As shown in FIG. 10, sensors are related to shipping containers for trucking, railroads, and marine shipping.

According to one embodiment, Sensor A can be located invisibly within the wall of a shipping container; the sensor will signal if it has been tampered with or if its status has integrity; it can differentially hold a record of how often and when the doors were opened and if target contents were removed. Target contents can be chemically tagged so that only Sensor A is able to detect the tag. According to one aspect, the sensor can accordingly identify if human smuggling is taking place. Alternatively, the sensor can identify if drugs are being shipped. Sensor B shows the sensor located in the door; this can be used as an anti-tampering report in real-time when the door is opened and the seal is broken. Sensor C shows the sensor at the seal of the door; this for example, can be used as an anti-tampering report in real-time when the door is opened and the seal is broken. Sensor D shows the sensor placed at the interface of the shipping truck and the container. The sensor will report in real-time if the seal is broken; and it may chemically sense and report in real-time if the container is exposed to any hazards from outside.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

The invention claimed is:

1. A fitting assembly for attachment to an end portion of a conduit, the fitting assembly comprising:
    a first component configured to receive the end portion of the conduit;
    a second component operably coupled to the first component, wherein the second component engages the first component to retain the end portion of the conduit in the first component, and
    an indicator carried by at least one of the first and second components, the indicator includes a miniature, micro or nano circuit having photovoltaic material to activate the circuit wherein the indicator provides an externally accessible indication of information related to a fluid flowing through the fitting assembly.

2. The fitting assembly of claim 1 wherein the indicator is a first leak indicator, and wherein the fitting assembly further comprises a plurality of leak indicators at different positions on the fitting assembly.

3. The fitting assembly of claim 2 wherein the first leak indicator provides a first type of indication that differs from a second type of indication provided by a second leak indicator.

4. The fitting assembly of claim 1 wherein the indicator is positioned to contact an exterior surface of the end portion of the conduit when the first component receives the end portion of the conduit.

5. The fitting assembly of claim 1 wherein the indicator is configured to chemically react with a fluid flowing through the fitting assembly when the fluid contacts the indicator.

6. The fitting assembly of claim 1 wherein the indication of information includes a visual indication of fluid leakage.

7. The fitting assembly of claim 6 wherein the visual indication includes the release of a liquid from the indicator.

8. The fitting of claim 7 wherein the liquid has a first color that differs from a second color of the fluid flowing through the fitting assembly.

9. The fitting assembly of claim 6 wherein the indicator reacts with the fluid flowing through the fitting assembly to provide the visual indication.

10. The fitting assembly of claim 1 wherein the indication of information includes at least one of a visual indication released by the indicator, an odor emitted by the indicator, and a radio signal transmitted by the indicator.

11. The fitting assembly of claim 1 wherein the indication of information is responsive to at least one of visible radiation, ultraviolet radiation, and microwave radiation directed at the fitting assembly.

12. The fitting assembly of claim 1 wherein the indication of information includes a radio signal emitted by the indicator.

13. The fitting assembly of claim 12 wherein the radio signal is provided in response to a change in at least one of capacitance, resistance, and magnetic field of the leak detector caused by a fluid flowing through the fitting assembly.

14. The fitting assembly of claim 1 wherein the indicator comprises circuitry configured to sense fluid leakage, and wherein the indication of fluid leakage includes a radio signal emitted by the circuitry of the indicator.

15. The fitting assembly of claim 14, further comprising a power source operably coupled to the detector.

16. The fitting assembly of claim 15 wherein the power source is a photovoltaic power source that is responsive to an external stimulus directed at the fitting assembly.

17. The fitting assembly of claim 1 wherein the indication of information includes a signal emitted by the indicator, wherein the signal includes information related to at least one of an amount of fluid leakage, the location of the fluid assembly, and the time of fluid leakage.

18. The fitting assembly of claim 1 wherein the indicator includes a hydrophobic portion and a hydrophilic portion.

19. The fitting assembly of claim 18 wherein conduit is configured to transfer water, and wherein the hydrophilic portion of the leak detector concentrates portions of water that contact the indicator to magnify the presence of the water on the leak detector.

20. The fitting assembly of claim 1 wherein at least a portion of the indicator includes titania.

21. The fitting assembly of claim 1 wherein the indicator includes a capillary assembly configured to concentrate at least a portion of the fluid.

22. A method of determining the early stages of a leak in a fitting assembly, the method comprising:
providing a conduit for conveying a fluid;
attaching a fitting assembly to the conduit, wherein the fitting assembly comprises a first component coupled to the conduit, a second component configured to engage the first component to retain the conduit within the first component, and a leak detector carried by at least one of the first and second components, the leak detector includes miniature, micro or nano circuitry activated by a photovoltaic material that is carried by the assembly proximate to the leak detector; and
flowing the fluid through the conduit and the fitting assembly, wherein if the fluid contacts the leak indicator the leak detector provides a warning in response to a fluid leakage from the fitting assembly.

23. The method of claim 22, further comprising providing a stimulus to the leak detector while flowing the fluid through the conduit.

24. The method of claim 23 wherein providing the stimulus includes directing at least one of visible radiation, ultraviolet radiation, and microwave radiation at the leak detector, and wherein the stimulus magnifies the warning.

25. The method of claim 22 wherein the warning comprises a visual indication of the fluid leakage.

26. The method of claim 22 wherein attaching the fitting assembly with the leak detector further comprises providing a sensor circuit carried by the fitting assembly, and wherein the warning includes a radio signal emitted from the sensor circuit.

27. A fluid conduit system comprising:
a first conduit configured for conveying a fluid;
a second conduit configured for conveying the fluid; and
a fitting assembly configured for coupling the first conduit to the second conduit for conveying the fluid there between, wherein the fitting assembly comprises
a first component configured to be attached to at least one of the first and second conduits;
a second component carried by the first component, wherein the second component engages the first component to retain the at least first and second conduit; and
a leak indictor carried by at least one of the first and second components, the leak indicator includes a sensor having miniature, micro or nano circuitry wherein the circuitry is activated by a photovoltaic material that is carried by the assembly proximate to the leak indicator, wherein the leak indicator provides a warning if the fluid leaks from the fitting assembly between the first and second conduits.

28. The fluid conduit assembly of claim 27 wherein:
the first component is a body having a first end portion opposite a second end portion, the first end portion being coupled to the first conduit and the second end portion being coupled to the second conduit;
the second component is a sleeve that is axially aligned with the body and disposed over at least a region of one of the first and second end portions.

29. The fluid conduit assembly of claim 27 wherein the leak indicator is positioned to contact at least one of the first and second conduits.

30. The fluid conduit assembly of claim 27 wherein the warning includes a visual indication that is externally accessible from the fitting assembly.

31. The fluid conduit assembly of claim 27 wherein the warning includes a radio signal transmitted from the fitting assembly to provide an alert to the fluid leakage.

32. The fluid conduit assembly of claim 27 wherein the warning is received in response to an interrogation stimulus directed at the fluid conduit assembly.

33. The fluid conduit assembly of claim 32 wherein the interrogation stimulus includes at least one of visible radiation, ultraviolet radiation, microwave radiation, infrared radiation, and a radio signal.

34. The fluid conduit assembly of claim 27 wherein the first and second conduits are a first set of conduits and the fitting assembly is a first fitting assembly associated with the corresponding first set of conduits, and wherein the fluid conduit assembly further comprises:
a plurality of sets conduits generally similar to the first set of conduits; and
a plurality of fitting assemblies, wherein each fitting assembly is generally similar to the first fitting assembly, and wherein individual fitting assemblies are associated with a corresponding set of conduits.

* * * * *